United States Patent
Gamache et al.

(10) Patent No.: US 6,174,878 B1
(45) Date of Patent: Jan. 16, 2001

(54) TOPICAL USE OF KAPPA OPIOID AGONISTS TO TREAT OTIC PAIN

(75) Inventors: Daniel A. Gamache, Arlington; John M. Yanni, Burleson, both of TX (US)

(73) Assignee: Alcon Laboratories, Inc., Fort Worth, TX (US)

(*) Notice: Under 35 U.S.C. 154(b), the term of this patent shall be extended for 0 days.

(21) Appl. No.: 09/387,359

(22) Filed: Aug. 31, 1999

Related U.S. Application Data

(63) Continuation-in-part of application No. 09/319,064, filed as application No. PCT/US97/23185 on Dec. 11, 1997.
(60) Provisional application No. 60/032,909, filed on Dec. 16, 1996.

(51) Int. Cl.$^7$ .................................................... A67K 31/55
(52) U.S. Cl. ........................ 514/211.12; 514/213.01; 514/411; 514/412; 514/433
(58) Field of Search ..................... 514/411, 412, 514/211.12, 213.01, 433

(56) References Cited

U.S. PATENT DOCUMENTS

| | | | |
|---|---|---|---|
| 4,871,865 | 10/1989 | Lever Jr., et al. | 313/12 |
| 4,923,892 | 5/1990 | Lever Jr., et al. | 313/12 |
| 5,049,669 | 9/1991 | Garret et al. | 514/226.2 |
| 5,270,050 | 12/1993 | Coquelet et al. | 424/427 |
| 5,688,955 | 11/1997 | Kruse et al. | 546/276.4 |

FOREIGN PATENT DOCUMENTS

| | | |
|---|---|---|
| 0 346 238 A1 | 12/1989 | (EP) . |
| 0 657 443 A1 | 6/1995 | (EP) . |
| WO 94/13275 A1 | 6/1994 | (WO) . |
| WO 98/26770 | 6/1998 | (WO) . |

OTHER PUBLICATIONS

Drugs Exptl. clin. Research XX(5) 171–174 (1995) Cottschlich et al.*

Barber, et al., "A pharmacological profile of the novel, peripherally–selective κ–opioid receptor agonist, EMD 61753", *British Journal Of Clinical Pharmacology*, vol. 113, No. 4, pp. 1317–1327 (1994).

DeHaven–Hudkins et al., "A Peripherally Slective Opiate Analgesic", *Society For Neuroscience*, vol. 22, pg. 1362, abstract No. 540.1 (1996).

Eisenberg, et al., "The peripheral antinociceptive effect of morphine in a rat model of facial pains",*Neuroscience*, vol. 72, No. 2, pp. 519–525 (1996).

*Goodman and Gilman's Pharmacological Basis of Therapeutics*(8th Edition), Jaffee, Chapter 21: "Opioid Analgesics And Antagonists", pp. 485–492 (1993).

Gottschlich, et al., "The peripherally acting k–opiate agonist EMD 61753 and analogues: opioid activity versus peripheral selectivity", *Drugs Exptl. Clin. Res.*, vol. XXI(5), pp. 171–174 (1995).

Joris et al., "Opiates suppress carrageenan–induced edema and hypothrmia at doses that inhibit hyperalgesia", *Pain*, vol. 43, No. 1, pp. 95–103 (1990).

Kanemasa, "κ–Opioid agonist U50488 inhibits P–type $Ca^{2+}$ channels by two mechanisms",*Brain Research*, vol. 707, pp. 207–212 (1995).

Karver, "Otitis Media", *Primary Care*, vol. 25, No. 3, pp. 619–632 (1998).

Ueda, et al., "Dual Effects of Dynorphin–1(1–13) on Cholinergic and Substance P–ergic Transmissions in the Rabbit Iris Sphincter Muscle", *J. Pharmacol. Exp. Ther.*, vol. 232, No. 2, pp. 545–550 (1985).

* cited by examiner

*Primary Examiner*—Zohreh Fay
(74) *Attorney, Agent, or Firm*—Michael C. Mayo; Patrick M. Ryan

(57) ABSTRACT

Compositions and methods for treating otic pain are disclosed. In particular, the invention discloses compositions and methods of using kappa opioid agonists locally for the prevention or alleviation of otic pain.

15 Claims, No Drawings

TOPICAL USE OF KAPPA OPIOID AGONISTS TO TREAT OTIC PAIN

This application is a continuation-in-part of U.S. patent application Ser. No. 09/319,064, filed May 27, 1999, and a 371 of PCT/US97/23185 filed Dec. 11, 1997. Priority is also claimed to Provisional application Ser. No. 60/032,909 filed Dec. 16, 1996.

The present invention relates to the pharmaceutical treatment of otic pain. In particular, the present invention relates to the topical use of kappa opioid receptor agonists and partial agonists for the prevention or alleviation of pain in the ear.

BACKGROUND OF THE INVENTION

Pain is a perceived nociceptive response to local stimuli in the body. The perception of pain at the level of the central nervous system requires the transmission of painful stimuli by peripheral sensory nerve fibers. Upon stimulation of tissue (i.e., thermal, mechanical or chemical), electrochemical signals are transmitted from the sensory nerve endings to the spinal column, and hence to the brain where pain is perceived.

The ear is highly innervated with sensory afferents capable of transmitting various painful stimuli to the central nervous system. The ear is comprised of outer, middle and inner ear portions and otic pain may arise in any of these portions of the ear. Pain conditions involving the ear, therefore, can arise in numerous instances, such as: foreign body stimulus, inflammation, edema, otic congestion, otic pressure, infection, accidental trauma, surgical procedures and post-surgical recovery.

The outer or "external" ear is comprised of the pinna and external ear canal ("EAC"). The EAC is a tubular, slightly curved structure extending from the pinna to the tympanic membrane or "ear drum." Sound travels through the EAC and causes the tympanic membrane to vibrate. Various disorders can arise in the outer ear eliciting pain to the host. For example, otitis externa is an acute, painful inflammatory condition of the EAC that affects all age groups of humans and accounts for roughly half of the ear pain pathologies known to exist. During the summer months, cases of otitis externa tend to increase due to what is known as "swimmer's ear." Swimmer's ear generally arises from the seepage of water into the EAC during swimming and the onset of infection and pain. Other outer ear disorders causing pain to the host include insertion of foreign objects in the ear, cerumen impaction, long-term use of hearing aids, and dermatological disorders, including psoriasis, eczema and seborrhea.

The middle ear is an air-filled cavity between the outer and inner ears. The middle ear is separated from the outer ear by the tympanic membrane and abuts the inner ear. It has a volume of about two milliliters and is connected to the back of the throat via the eustachian tube. The middle ear contains the malleus, icus and stapes, which are tiny bones that translate the movement of the tympanic membrane to the inner ear. Various conditions of the middle ear can cause pain to the host. For example, otitis media, which can be acute ("AOM") or associated with effusion ("OME"), is an inflammatory condition of the middle ear which generally affects children more often than adults (Karver, Otitis Media, *Primary Care*, Volume 25, No. 3, pages 619–632 (1998). The etiology of otitis media is fairly broad and can be caused by various inflammatory events including infection and allergy. Effusion, which can be sterile or contain infectious material, may also result from otitis media. The fluid consists of various inflammatory cells (white blood cells), mediators of allergy and inflammation and cellular debris.

The inner ear comprises the sensory organs of the auditory and vestibular systems. It consists of two major compartments, known as the bony and membranous labyrinths. These chambers are highly organized and sensitive tissues and provide both auditory perception and balance to the animal. Various pathologies may arise in the inner ear, creating distortion of hearing, loss of balance and pain.

Since otic pain is often associated with infection and resultant congestion and pressure, the primary therapeutic approach to treating otic pain is the administration of antiobiotics, both systemically and topically.

Various other therapies have been attempted for the alleviation of otic pain. Topical steroids (e.g., hydrocortisone) and systemic non-steroidal anti-inflammatory drugs (NSAIDs), such as aspirin and ibuprofen, have been used typically in conjunction with anti-infectives to treat otic pain.

Local anesthetics are another class of compounds which relieve pain by directly inhibiting nerve cellular function. A drawback of local anesthetic therapy is the short duration of action of such drugs. Another problem with the use of local anesthetics is that their mechanism of action, non-specific membrane stabilization, can have the undesired coincident effect of also inhibiting biological functions of cells, such as fibroblasts and surrounding neural cells. Therefore, even though pain sensation can be abated with local anesthetic treatment, healing and normal function of the tissue may be significantly compromised. There is a need, therefore, to discover agents which potently and specifically inhibit the transmission of painful stimuli by sensory afferents, following local otic application.

Other agents have also been suggested for use in treating pain. Such agents include tricyclic antidepressants such as imipramine and desipramine, alpha-2 adrenergic agonists, serotonin uptake blockers, such as prozac, and other analgesics such as paracetamol, as described in U.S. Pat. No. 5,270,050 (Coquelet et al.). Some of these therapies, however, have been associated with side-effects such as dryness of mouth, drowsiness, constipation, and low potencies and efficacies.

Opiates are a class of compounds with well documented clinical analgesic efficacy. Opiates can be administered in a number of ways. For example, opiates can be administered systematically, by intravenous injection or oral dosage, or locally, by subcutaneous, intramuscular or topical application. Systemic administration of opiates, however, has been associated with several problems including dose escalation (tolerance), addiction, respiratory depression and constipation.

"Opioids" is a generic term of art used to describe molecules that produce morphine-like activity in the body. There are three major categories of opioid receptors, designated $\mu$ (mu), $\kappa$ (kappa) and $\delta$ (delta). Other sub-type receptors appear to exist as well. Opioid receptors have been differentiated among each other by the preferential binding affinities of different agonists and antagonists, and by the different responses obtained from each receptor's binding. For example, the full agonist morphine has a ten times greater affinity for the mu receptor than for the delta and kappa receptors. Thus, morphine is a mu agonist (See, *Goodman and Gilman's Pharmacological Basis of Therapeutics* (8th Edition), Jaffee, Chapter 21: Opioid Analgesics And Antagonists, page 485–492 (1993).) Kappa receptors have also been delineated from the general class of opioid receptors by the fact that mu and delta receptor agonists increase membrane potassium conductance and decrease the duration of presynaptic action potential, whereas kappa receptor agonists decrease voltage-dependent calcium conductance without affecting potassium conductance (Kanemasa, k-opioid agonist U50488 inhibits P-type $Ca^{2+}$ channels by two mechanisms, *Brain Research*, volume 707, pages 207–212 (1995)).

While it is known that opiate analgesics such as morphine relieve pain by activating specific receptors in the brain, recent studies demonstrate the analgesic effects of compounds which act on kappa receptors in peripheral tissue. (See, Joris et al., Opiates suppress carrageenan-induced edema and hypothermia at doses that inhibit hyperalgesia, Pain, volume 43, pages 95–103 (1990); Eisenberg, The peripheral antinociceptiave effect of morphine in a rat model offacial pains, *Neuroscience*, volume 72, No. 2, pages 519–575 (1996); and Gohschlich, The peripherally acting k-opiate agonist EMD 61753 and analogues: opioid activity versus peripheral selectivity, *Drugs Exptl. Clin. Res.*, volume XX1(5), pages 171–174 (1995)).

Nowhere in the art, however, has it been described to use kappa opioid agonists to treat otic pain.

SUMMARY OF THE INVENTION

The present invention is directed to compositions and methods of treating otic pain. The present invention is based in part on the finding that kappa opioid receptor agonists have analgetic activity in peripheral tissues when administered locally. More specifically, the present invention provides compositions containing kappa opioid agonists for the treatment of otic pain. The present invention is also directed to compositions comprising combinations of kappa opioid receptor agonists and other pharmaceutical agents (i.e., antimicrobial agents, antiinflammatory agents or anti-allergy agents) and methods of use.

The methods of the present invention involve the topical otic or intranasal application of the compositions of the present invention. One advantage of this therapy is that the inhibition of pain is receptor-specific, as contrasted with non-specific therapy, such as local anesthetic treatment. This specific activity may reduce greatly the number of dosings per day, and also reduce the drawbacks of short duration of action and inhibition of wound healing, which are associated with local anesthetics. Additionally, kappa opioid receptor agonists which act locally would minimize the potential for sedation, tolerance, addiction and constipation associated with the chronic, systemic administration of opiates.

DETAILED DESCRIPTION OF THE INVENTION

The present invention is directed to the use of kappa opioid receptor agonists for the prevention or alleviation of otic pain. It is believed that kappa opioid agonists prevent or alleviate otic pain. The kappa opioid receptor is found principally in the spinal cord, but recent evidence of other peripherally located kappa receptors has been reported, as described above.

The compounds of the present invention are kappa opioid receptor agonists. As used herein, a "kappa opioid agonist" refers to a compound which activates a kappa opioid receptor and at concentrations lower than those needed to activate other opioid receptors. The kappa opioid receptor agonists of the present invention are known or may be elucidated by various biological binding studies known in the art. For example, the kappa opioid agonists of the present invention may be ascertained by displacement studies involving the binding of known radioactive agonists, such as U69593, with target tissue slices or homogenates (Gohschlich, *Drugs Exptl. Clin. Res.*, Volume XX1 (5), pages 171–174 (1995)).

The following compounds are examples of kappa opioid agonists, listed as their trade name and/or number: 4-Benzofuranacetamide,N-methyl-N-[7-(1-pyrrolidinyl)-1-oxaspiro[4.5]dec-8-yl]-, monohydrochloride,[5R-(5alpha,7alpha,8beta)]-[CAS] (enadoline); Benzeneacetamide, 3,4-dichloro-N-methyl-N-[1-phenyl-2-(1-pyrrolidinyl)ethyl]-, monohydrochloride, (S)-[CAS] (ICI-199441); Thiomorpholine,4-[(5,6-dichloro-2,3-dihydro-1H-inden-1-yl)carbonyl]-3-(1-pyrrolidinylmethyl)-, monohydrochloride, [R-(R*,S*)]-[CAS] (R-84760); Piperidine, 2-(1-pyrrolidinylmethyl)-1-[[4-(trifluoromethyl)phenyl]acetyl]-, monohydrochloride, (S)-[CAS] (ZT-52656A); 3-Thiophenecarboxamide,N-[[5-(2-fluorophenyl)-2,3-dihydro-1-methyl-1H-1,4-benzodiazepin-2-yl]methyl]-[CAS] (tifluadom); Benzo[b]thiophene-4-acetamide, N-methyl-N-[2-(1-pyrrolidinyl)cyclohexyl]-, monohydrochloride, trans-(+/−)-[CAS] (PD-117302); PD-129290; 2,6-Methano-3-benzazocin-8-ol,1,2,3,4,5,6-hexahydro-6,11-dimethyl-3-[(2-methyl-3-furanyl)methyl]-,(2alpha,6alpha,11R*)-(+/−)-[CAS] (MR-1268); Morphinan-3-ol,6-(acetylthio)-17-(cyclopropylmethyl)-7,8-didehydro-4,5-epoxy-, acetate(ester), (5alpha,6beta)-[CAS] (KT-90); 1,4-Dioxa-8-azaspiro[4.5]decane,8-[(3,4-dichlorophenyl)acetyl]-7-(1-pyrrolidinylmethyl)-, monohydrochloride[CAS] (GR-45809); 1-Piperazinecarboxylic acid,4-[(3,4-dichlorophenyl)acetyl]-3-(1-pyrrolidinylmethyl)-, methyl ester,(E)-2-butenedioate [CAS] (GR-89696); (R)-methyl-4-[(3,4-dichlorophenyl)acetyl]-3-(1-pyrrolidinyl-methyl)-1-piperazinecarboxylate fumarate (GR-103545); Piperazine,4-acetyl-1-[(3,4-dichlorophenyl)acetyl]-2-[(3-hydroxy-1-pyrrolidinyl)methyl]-[CAS] (GR-94839); Morphinan-3-ol, 17-(cyclobutylmethyl)-8-methyl-6-methylene-, (8beta)-[CAS] (xorphanol); Benzeneacetamide,N-[2,3-dihydro-2-(1-pyrrolidinyl)-1H-inden-1-yl]-N-methyl-3-nitro-, monohydrochloride, trans-(+/−)-[CAS] (RU-49679); Benzenemethanamine,alpha-ethyl-N,N-dimethyl-alpha-[[(3,4,5-trimethoxyphenyl) methoxy]methyl]-, (R)-[CAS] (fedotozine); Benzeneacetamide,3,4-dichloro-N-methyl-N-[1,2,3,4-tetrahydro-5-methoxy-2-(1-pyrrolidinyl)-1-naphthalenyl]-, trans-(+/−)-[CAS] (DuP-747); (E)-4,5-dichloro-N-methyl-N-[2-[1-pyrrolidinyl]cyclohexyl]-2-thiopheneacetamide HCl (HN-11608); RP-60180; U-62066; Benzeneacetamide,3,4-dichloro-N-methyl-N-[7-(1-pyrrolidinyl)-1-oxaspiro[4.5]dec-8-yl]-,(5alpha,7alpha,8beta)-(+/−)-[CAS] (spiradoline), and Benzeneacetamide, 3,4-dichloro-N-methyl-N-[2-(1-pyrrolidinyl)cyclohexyl]-, trans-(+/−)-, monomethanesulfonate [CAS] (U-50488). Preferred kappa opioid compounds of the present invention are those which only act in the periphery and do not cross the blood-brain barrier, or have limited CNS effects, such as Benzeneacetamide,2-amino-N-[2-(3-hydroxy-1-pyrrolidinyl)-1-phenylethyl]-N-methyl-, [S-(R*,R*)]-[CAS] (EMD-60400); and Benzeneacetamide,N-[2-(3-hydroxy-1-pyrrolidinyl)-1-phenylethyl]-N-methyl-.alpha.-phenyl-,[S-(R*,R*)]-[CAS] (EMD 61753). The most preferred kappa opioid agonist is EMD-61753. The kappa opioid agonists of the present invention are available from commercial sources or may be synthesized by methods known to those skilled in the art.

The kappa opioid agonists of the present invention will be contained in topical or intranasal compositions, in accordance with formulation techniques known to those skilled in the art. The compounds may be included in solutions, suspensions, aerosols and other dosage forms adapted for the particular kappa opioid agonist and dosing regimen.

The kappa opioid agonists will be contained in compositions of the present invention in concentrations effective to prevent or ameliorate otic pain. As used herein, the term "pharmaceutically effective amount" refers to that amount of one or more kappa opioid agonists which prevents or alleviates otic pain. In general, the dosage of kappa opioid agonists utilized for any of the uses described herein will be from about one to two drops of a 0.01 to 3% weight/volume ("w/v") composition or corresponding amount for aerosol application, administered one to four times per day.

The present invention is particularly directed to the provision of compositions adapted for topical treatment of otic tissues. The compositions may also be adapted for administration intranasally for treatment of otic tissues, such as nasal drops or an aerosol composition. The otic compositions of the present invention will include one or more kappa opioid agonists and a pharmaceutically acceptable vehicle for these agonist(s). Various types of vehicles may be used. The vehicles will generally be aqueous in nature. Aqueous solutions or suspensions are generally preferred, based on ease of formulation, as well as a patient's ability to easily administer such compositions by means of instilling one to two drops of the solutions in the affected ears. However, the compounds of the present invention may also be readily incorporated into other types of compositions, such as aerosols (intranasal or intraotic), suspensions, viscous or semi-viscous gels or other types of solid or semi-solid compositions. Suspensions may be preferred for kappa opioid agonists which are relatively insoluble in water.

As stated above, the compositions of the present invention may also contain additional pharmaceutically active agents or may be dosed concurrently with other pharmaceutical compositions.

In particular, when treating a mammal for the prevention, treatment or amelioration of otic infection, the compositions of the present invention may also contain one or more antibiotic, antiviral and/or antifungal agents (hereinafter collectively referred to as "antimicrobial agents") or may be dosed concurrently or sequentially with antimicrobial agent containing compositions. Examples of antimicrobial agents include, but are not limited to, chloremphenicol, ofloxacin, norfloxacin, lomefloxacin, ciprofloxacin, natamycin, neomycin, polymyxin B, gentamycin, tobramycin, bacitracin, gramicidin, erythromycin, moxifloxacin, oxazolidinones, trovafloxacin, grepafloxacin, sulfacetamide, tetracycline, sulfisoxazole, diolamine, trifluorothymidine, acyclovir, gancyclovir, vaniomycin or other antibiotic, antiviral and antifungal agents known to those skilled in the art. The kappa opioid agonist/antimicrobial agent combination compositions will contain one or more kappa opioids agonists, as stated above, and one or more antimicrobial agents in an amount effective to prevent, treat or ameliorate otic infection. As used herein, such an amount is referred to as "an effective amount of one or more antimicrobial agents" or "an amount effective to prevent, treat or ameliorate otic infection." In general, however, the kappa opioid agonist/antimicrobial combination compositions of the present invention will typically contain one or more antibiotics in an amount of about 0.05 to 3.0% w/v.

When treating a mammal for the prevention, treatment or amelioration of otic allergic reactions and responses, the compositions of the present invention may also contain one or more anti-allergy agents, histamine $H_1$ receptor antagonists or anti-histaminic agents (hereinafter collectively referred to as "anti-allergy agents"), or may be dosed concurrently or sequentially with anti-allergy agent containing compositions. Examples of anti-allergy agents include, but are not limited to, mizolastine, mapinastine, levocabastine, pheniramine, antazoline, ketotifen, azelastine, doxepine analogs, such as those described in U.S. Pat. No. 4,871,865 (Lever et al.) and U.S. Pat. No. 4,923,892 (Lever et al.), cetirizine, loratadine, fenoxifenadine, diphenhydramine, brompheniramine, chlorpheniramine, clemastine, pyrilamine, cromolyn, nedocromil, lodoxamide, or other anti-allergy agents known to those skilled in the art. The kappa opioid agonist/anti-allergy agent combination compositions will contain one or more kappa opioid agonists, as stated above, and one or more anti-allergy agents in an amount effective to prevent, treat or ameliorate otic allergic reactions and responses. As used herein, such an amount is referred to as "an effective amount of one or more anti-allergy agents" or "an amount effective to prevent, treat or ameliorate otic allergic reactions or responses." In general, however, the kappa opioid agonist/anti-allergy agent combination compositions of the present invention will typically contain one or more anti-allergy agents in an amount of about 0.001 to 1.0% w/v.

When treating a mammal for the prevention, treatment or amelioration of otic inflammatory reactions and responses, the compositions of the present invention may also contain one or more anti-inflammatory agents or may be dosed concurrently or sequentially with anti-inflammatory agent containing compositions. Examples of anti-inflammatory agents include, but are not limited to, PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A, CT-2820, PD-168787, CP-293121, DWP-205297, CP-220629, SH-636, BAY-19-8004, and roflumilast; cyclooxygenase type I and II inhibitors, such as nepafenac, amfenac, diclofenac, flurbiprofen, indomethacin, naproxen, ketorolac, ibuprofen, bromfenac, ketoprofen, meclofenamate, piroxicam, sulindac, suprofen, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, darbufelone mesylate, L-804600 and S-33516; and inhibitors of cytokine production, such as inhibitors of the NFkB transcription factor; or other anti-inflammatory agents known to those skilled in the art. The kappa opioid agonist/anti-inflammatory agent combination compositions will contain one or more kappa opioid agonists, as stated above, and one or more anti-inflammatory agents in an amount effective to prevent, treat or ameliorate otic inflammatory reactions or responses. As used herein, such an amount is referred to as "an effective amount of one or more anti-inflammatory agents" or "an amount effective to prevent, treat or ameliorate otic inflammatory reactions and responses." In general, however, the kappa opioid agonist/anti-inflammatory agent combination compositions of the present invention will typically contain one or more anti-inflammatory agents in an amount of about 0.01 to 1.0% w/v.

The otic compositions of the present invention may also include various other ingredients, such as buffers, preservatives, co-solvents and viscosity building agents.

An appropriate buffer system (e.g., sodium phosphate, sodium acetate or sodium borate) may be added to the compositions to prevent pH drift under storage conditions.

Otic products are typically packaged in multidose form. Preservatives are thus required in multidose compositions to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v.

Some of the compounds of the present invention may have limited solubility in water and therefore may require a surfactant or other appropriate co-solvent in the composition. Such co-solvents include: polyethoxylated castor oils, Polysorbate 20, 60 and 80; Pluronic® F-68, F-84 and P-103 (BASF Corp., Parsippany N.J., USA); cyclodextrin; or other agents known to those skilled in the art. Such co-solvents are typically employed at a level of from 0.01 to 2% w/v.

Viscosity greater than that of simple aqueous solutions may be desirable to increase otic absorption of the active compound, to decrease variability in dispensing the formulations, to decrease physical separation of components of a suspension or emulsion of formulation and/or otherwise to improve the otic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2% w/v.

The compositions may also be used for treating irritated tissues following otic surgery. The compositions may be used for acute treatment of temporary conditions, or may be administered chronically. The compounds may also be used prophylactically, especially prior to otic surgery or noninvasive otic procedures, or other types of surgery.

The compounds and compositions of the present invention will be used to prevent or ameliorate otic pain associated with various stimuli. For example, the kappa opioid agonists and compositions of the present invention may be used in treating pain arising from allergens, inflammation, trauma, congestion, infection, foreign body sensation and surgery, e.g., following cochlea implant surgery. With such treatment, the kappa opioid agonists can be individually dosed, or in combination with other pharmaceutical agents known in the art, e.g., an antibiotic.

The compositions of the present invention are further illustrated by the following formulation Examples 1–4. The ingredient "kappa opioid agonist" denotes a compound of the present invention.

EXAMPLE 1

The following is an example of an otic/nasal solution:

| Ingredient | Amount (% w/v) |
| --- | --- |
| EMD-61753 | 0.01–1.0 |
| Phosphate Buffered Saline | 1.0 |
| Polysorbate 80 | 0.5 |
| Purified water | q.s. to 100% |

EXAMPLE 2

The following is an example of an otic/nasal suspension:

| Ingredient | Amount (% w/v) |
| --- | --- |
| kappa opioid agonist | 0.01–1.0 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 3

The following is an example of an otic/nasal suspension or solution:

| Ingredient | Amount (% w/v) |
| --- | --- |
| kappa opioid agonist | 0.01–1.0 |
| Phosphate Buffered Saline | 1.0 |
| Hydroxypropyl-β-cyclodextrin | 4.0 |
| Purified water | q.s. to 100% |

EXAMPLE 4

The following is an example of an otic/nasal suspension:

| Ingredient | Amount (% w/v) |
| --- | --- |
| Kappa opioid agonist | 0.1–1.0 |
| Moxifloxacin | 0.3 |
| Benzalkonium Chloride | 0.01 |
| Edetate Disodium, USP | 0.01 |
| Sodium Chloride, USP | 0.3 |
| Sodium Sulfate, USP | 1.2 |
| Tyloxapol, USP | 0.05 |
| Hydroxyethylcellulose | 0.25 |
| Sulfuric Acid and/or Sodium Hydroxide, NF | q.s. |
| Purified Water, USP | q.s. to 100% |

What is claimed is:

1. A method for treating otic pain which comprises administering to a mammal a topical or intranasal composition comprising a pharmaceutically effective amount of one or more kappa opioid agonist(s) in a pharmaceutically acceptable vehicle.

2. A method according to claim 1, wherein the kappa opioid agonist is selected from the group consisting of: asimadoline (EMD-61753); enadoline; benzeneacetamide, 3,4-dichloro-N-methyl-N-[1-phenyl-2-(1-pyrrolidinyl) ethyl]-, monohydrochloride, (S)-[CAS] (ICI-199441); thiomorpholine,4-[(5,6-dichloro-2,3-dihydro-1H-inden-1-yl)carbonyl]-3-(1-Pyrrolidinylmethyl)-, monohydrochloride, [R-(R*,S*)]-[CAS] (R-84760); piperidine, 2-(1-pyrrolidinylmethyl)-1-[[4-(trifluoromethyl) phenyl]acetyl]-, monohydrochloride, (S)-[CAS] (ZT-52656A); tifluadom; benzo[b]thiophene-4-acetamide, N-methyl-N-[2-(1-pyrrolidinyl)cyclohexyl]-, monohydrochloride, trans-(+/−)-[CAS] (PD-117302);

4-benzofuranacetamide,N-methyl-N-[7-(1-pyrrolidinyl)-1-oxaspiro[4.5]dec-8-yl]-, monohydrochloride, [5R-(5.alpha., 7.alpha.,8.beta.)]-[CAS] (PD-129290); 2,6-methano-3-benzazocin-8-ol,1,2,3,4,5,6-hexahydro-6,11-dimethyl-3-[(2-methyl-3-furanyl)methyl]-,(2alpha,6alpha,11R*)-(+/−)-[CAS] (MR-1268); morphinan-3-ol,6-(acetylthio)-17-(cyclopropylmethyl)-7,8-didehydro-4,5-epoxy-, acetate (ester), (5alpha,6beta)-[CAS] (KT-90); 1,4-dioxa-8-azaspiro[4.5]decane,8-[(3,4-dichlorophenyl)acetyl]-7-(1-pyrrolidinylmethyl)-, monohydrochloride[CAS] (GR-45809); 1-piperazinecarboxylic acid,4-[(3,4-dichlorophenyl)acetyl]-3-(1-pyrrolidinylmethyl)-, methyl ester,(E)-2-butenedioate [CAS] (GR-89696); (R)-methyl-4-[(3,4-dichlorophenyl)acetyl]-3-(1-pyrrolidinyl-methyl)-1-piperazinecarboxylate fumarate (GR-103545); piperazine,4-acetyl-1-[(3,4-dichlorophenyl)acetyl]-2-r(3-hydroxy-1-pyrrolidinyl)methyl]-[CAS] (GR-94839); xorphanol; benzeneacetamide,N-[2,3-dihydro-2-(1-pyrrolidinyl)-1H-inden-1-yl]-N-methyl-3-nitro-, monohydrochloride, trans-(+/−)-[CAS] (RU-49679); fedotozine; benzeneacetamide,3,4-dichloro-N-methyl-N-[1,2,3,4-tetrahydro-5-methoxy-2-(1-pyrrolidinyl)-1-naphthalenyl]-, trans-(+/−)-[CAS] (DuP-747); (E)-4,5-dichloro-N-methyl-N-[2-[1-pyrrolidinyl]cyclohexyl]-2-thiopheneacetamide HCl (HN-11608); apadoline (RP-60180); spiradoline (U-62066); and benzeneacetamide, 3,4-dichloro-N-methyl-N-[2-(1-pyrrolidinyl)cyclohexyl]-, trans-(+/−)-, monomethane-sulfonate [CAS] (U-50488).

3. A method according to claim 2, wherein the kappa opioid agonist is asimadoline (EMD-61753).

4. A method according to claim 1, further comprising administering the composition topically to the ear or intranasally.

5. A method according to claim 2, further comprising administering the composition topically to the ear or intranasally.

6. A method according to claim 1, wherein the otic pain is the result of otitis media, otitis externa, otic surgery or swimmer's ear.

7. A method according to claim 1, wherein the composition further comprises one or more anti-microbial agents in an amount effective to prevent, treat or ameliorate otic infections.

8. A method according to claim 1, wherein the composition further comprises one or more anti-allergy agents in an amount effective to prevent, treat or ameliorate otic allergic reactions or responses.

9. A method according to claim 1, wherein the composition further comprises one or more anti-inflammatory agents in an amount effective to prevent, treat or ameliorate otic inflammatory reactions or responses.

10. A method according to claim 7, wherein the anti-microbial agent(s) is/are selected from the group consisting of: chloremphenicol, ofloxacin, norfloxacin, lomefloxacin, ciprofloxacin, natamycin, neomycin, polymyxin B, gentamycin, tobramycin, bacitracin, gramicidin, erythromycin, moxifloxacin, oxazolidinones, trovafloxacin, grepafloxacin, sulfacetamide, tetracycline, sulfisoxazole, diolamine, trifluorothymidine, acyclovir, gancyclovir and vaniomycin.

11. A method according to claim 8, wherein the anti-allergy agent(s) is/are selected from the group consisting of: mizolastine, mapinastine, levocabastine, pheniramine, antazoline, ketotifen, azelastine, doxepine analogs, cetirizine, loratadine, fenoxifenadine, diphenhydramine, brompheniramine, chlorpheniramine, clemastine, pyrilamine, cromolyn, nedocromil and lodoxamide.

12. A method according to claim 9, wherein the anti-inflammatory agent(s) is/are selected from the group consisting of: PAF antagonists; PDE IV inhibitors; cyclooxygenase type I and II inhibitors; cyclooxygenase type II selective inhibitors; and inhibitors of cytokine production.

13. A method according to claim 12, wherein the PAF antagonists are selected from the group consisting of foropafant (SR-27417), 4-ethynyl-3-[3-fluoro-4-(2-methyl-1H-imidazo[4,5-c]pyridin-1-ylmethyl)benzoyl]-N,N-dimethylindole-1-carboxamide hydrochloride (A-137491), pyridinium, 1-((acetyloxy)methyl)-3-(7-((1-((dimethylamino)carbonyl)-6-(4-fluorophenyl)-1H-indol-3-yl)carbonyl)-1H-pyrrolo[1,2-c]thiazol-3-yl), chloride, (R)-[CAS] (ABT-299), apafant, bepafant, minopafant, (S)-(+)-6-(2-chlorophenyl)-3-cyclopropanecarbonyl-8,11-dimethyl-2,3,4,5-tetrahydro-8H-pyrido-[4',3':4,5]thieno[3,2-f][1,2,3], (S)-[CAS] (E-6123), 6-(2-chlorophenyl)-7,10-dihydro-N-(4-methoxyphenyl)-1-methyl-4H-pyrido[4',3'-4,5]thieno[3,2-f][1,2,4]triazolo[4,3-a][1,4]diazepine-9(8H)-carboxamide (BN-50727), nupafant and modipafant; the PDE IV inhibitors are selected from the group consisting of ariflo, torbafylline, rolipram, filaminast, piclamilast, cipamfylline, 3-[3-(cyclopentyloxy)-4-methoxvbenzyl]-6-(ethylamino)-8-isopropyl-3H-purinehydrochloride (V-1 1294A), (3R)-N-(9-Methyl-4-oxo-1-phenyl-3,4,6,7-tetrahydro[1,4]diazepino[6,7,1-hi]indol-3-yl)isonicotinamide (PD-168787), (S)-3-(3-Cyclopentyloxy-4-methoxy)phenyl-2-isoxazoline-5-hydroxamic acid (CP-293121), 1-cyclopentyl-3-ethyl-6-(2-methylphenyl)-7-oxo-4,5,6,7-tetrahydro-1H-pyrazolo[3,4-c]pyridine (CP-220629), and roflumilast; the cyclooxygenase type I and II inhibitors are selected from the group consisting of nepafenac, amfenac, diclofenac, flurbiprofen, indomethacin, naproxen, ketorolac, ibuprofen, bromfenac, ketoprofen, meclofenamate, piroxicam, sulindac, suprofen, mefanamic acid, diflusinal, oxaprozin, tolmetin, fenoprofen, benoxaprofen, nabumetome, etodolac, phenylbutazone, aspirin, oxyphenbutazone, benzoic acid, 2-(acetyloxy)-, 2-((nitrooxy)methyl)phenyl ester [CAS] (NCX-4016), nitroflurbiprofen (HCT-1026), NO-diclofenac (NCX-284), 4-Nitrobutyl 5-amino-2-hydroxybenzoate (NCX-456), tenoxicam and carprofen; the cyclooxygenase type II selective inhibitors are selected from the group consisting of methanesulfonamide,N-[2-(cyclohexyloxy)-4-nitrophenyl]-[CAS] (NS-398), vioxx, celecoxib, etodolac, darbufelone mesylate, and 2-Benzyl-4-isopropoxy-5-(4-methanesulfonylphenyl)pyridazin-3-one(L-804600); and the inhibitors of cytokine production are selected from the group consisting of inhibitors of the NFkB transcription factor.

14. A method according to claim 7, wherein the otic pain is caused by otitis media, otitis externa, otic surgery or swimmer's ear.

15. A method according to claim 10, wherein the otic pain is caused by otitis media, otitis externa, otic surgery or swimmer's ear.

* * * * *